United States Patent [19]
Bryant et al.

[11] Patent Number: 5,994,370
[45] Date of Patent: Nov. 30, 1999

[54] INDENE COMPOUNDS HAVING ACTIVITY AS SERMS

[75] Inventors: Henry Uhlman Bryant; Charles David Jones; Pamela Ann Pennington, all of Indianapolis, Ind.

[73] Assignee: Eli Lilly and Company, Indianapolis, Ind.

[21] Appl. No.: 09/064,548

[22] Filed: Apr. 22, 1998

Related U.S. Application Data

[60] Provisional application No. 60/044,923, Apr. 25, 1997.

[51] Int. Cl.$^6$ .................. A61K 31/445; A61K 31/55; C07D 211/06; C07D 207/08
[52] U.S. Cl. .................. 514/319; 514/212; 514/428; 514/651; 540/609; 546/205; 548/566; 564/347
[58] Field of Search ................. 540/609; 546/205; 548/566; 564/347; 514/212, 319, 428, 651

[56] References Cited

U.S. PATENT DOCUMENTS

| | | | |
|---|---|---|---|
| 3,274,213 | 9/1966 | Lednicer et al. | 546/205 |
| 3,394,125 | 7/1968 | Crenshaw | 548/525 |
| 3,413,305 | 11/1968 | Crenshaw | 548/525 |
| 3,483,293 | 12/1969 | Duncan et al. | 514/428 |
| 4,133,814 | 1/1979 | Jones et al. | 546/202 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 4,729,999 | 3/1988 | Young | 514/227 |
| 4,894,373 | 1/1990 | Young | 514/239.2 |
| 5,147,880 | 9/1992 | Jones et al. | 514/650 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |
| 5,484,795 | 1/1996 | Bryant et al. | 514/212 |

FOREIGN PATENT DOCUMENTS

| | | |
|---|---|---|
| 062 503 | 10/1982 | European Pat. Off. . |
| WO 89/0289 | 4/1989 | WIPO . |
| WO 95/10513 | 4/1995 | WIPO . |

OTHER PUBLICATIONS

Crenshaw, R.R., et al, *J. Med. Chem* 14(12):1185–1190 (1971).

Jones, C.D. et al, *J. Med. Chem.* 27:1057–1066 (1984).

Jones, C.D., et al, *J. Med. Chem.*, 35: 931–938 (1992).

*Primary Examiner*—Ceila Chang
*Attorney, Agent, or Firm*—Gilbert T. Voy

[57] ABSTRACT

The present invention provides a class of substituted indene compounds and their pharmaceutically acceptable salts which possess selective estrogen receptor modulator (SERM) activity and are thus useful in the treatment of osteoporosis and cardiovascular disease, particularly hyperlipidemia in women. The compounds possess the structure

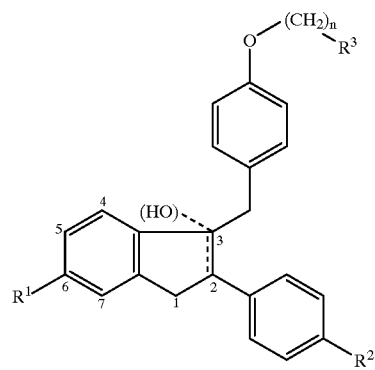

in which $R^1$ is hydrogen, hydroxy, alkoxy, phenylcarbonyloxy, alkylcarbonyloxy, or alkylsulfonyloxy. $R^2$ is hydrogen, hydroxy, halo, alkoxy, phenylcarbonyloxy, alkylcarbonyloxy, or alkylsulfonyloxy. $R^3$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexa-methyleneimino, and n is 2 or 3. The dashed line bond between the carbon atoms at positions 1 and 2 of the indene nucleus represent an optional double bond with the proviso that when the double bond is absent, the parenthetic hydroxy group at position 1 is present and vice versa. Certain 2,3-dihydro-1H-indene precursors to the disclosed indene compounds also possess SERM activity and are useful for the same purposes.

12 Claims, No Drawings

INDENE COMPOUNDS HAVING ACTIVITY AS SERMS

CROSS-REFERENCE TO RELATED APPLICATIONS

This application claims priority to provisional application Ser. No. 60/044,923 filed Apr. 25, 1997.

TECHNICAL FIELD

This invention relates to compounds having pharmacological activity, to compositions containing the compounds, and to medical methods of treatment. More particularly, this invention concerns a class of substituted 1H-indene and 2,3-dihydro-1H-indene compounds having activity as selective estrogen receptor modulators ("SERM's"), to pharmaceutical formulations comprising the compounds, and to methods of employing the compounds in the treatment of osteoporosis and cardiovascular disease conditions, particularly hyperlipidemia.

BACKGROUND OF THE INVENTION

Menopause, the transition in women from the reproductive to the non-reproductive stage of life, is characterized by the cessation of menstruation and occurs at an average age of fifty years. The postmenopausal state is characterized by changes in the levels of circulating sex hormones, the most dramatic of which is the reduction in plasma levels of 17β-estradiol to less than ten percent of premenopausal values. Clinical and epidemiological studies have shown that the postmenopausal state is an important risk factor for a number of chronic disorders, notably osteoporosis and cardiovascular disease. In view of the fact that the current life span of women is about eighty years, women spend approximately one-third of their lives in the postmenopausal state. This means that the potential for chronic effects of the postmenopausal state on women's health is greater today than at the turn of the century when life expectancy was considerably shorter.

Osteoporosis describes a group of diseases which are characterized by the net loss of bone mass per unit volume. The consequence of this loss of bone mass and resulting bone fracture is the failure of the skeleton to provide adequate structural support for the body. The most vulnerable bone tissue to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the biomechanical strength of the overall structure.

Following the cessation of menses, most women lose from about 20% to about 60% of the bone mass in the trabecular compartment of the bone within 3 to 6 years. This rapid loss is generally associated with an increase of bone resorption and formation. However, the resorptive cycle is more dominant and the result is a net loss of bone mass.

In postmenopausal osteoporosis, it is primarily the net resorption and loss of the trabeculae which leads to the failure and fracture of bone. In light of the loss of the trabeculae in postmenopausal women, it is not surprising that the most common fractures are those associated with bones which are highly dependent on trabecular support, for example the vertebrae, the neck, and the weight bearing bones such as the femur and the fore-arm. Indeed, hip fracture, collies fractures, and vertebral crush fractures are hallmarks of postmenopausal osteoporosis.

There are an estimated 25 million women in the United States alone who are afflicted with this disease. The results of osteoporosis are personally harmful and also account for a large economic loss due its chronicity and the need for extensive and long term support (hospitalization and nursing home care). This is especially true in more elderly patients. Additionally, although osteoporosis is not generally thought of as a life threatening condition, a 20% to 30% mortality rate is related with hip fractures in elderly women. A large percentage of this mortality rate can be directly associated with postmenopausal osteoporosis.

Cardiovascular disease is the leading cause of death among women. Compared to men, premenopausal women are relatively protected from cardiovascular disease; however, this protection is gradually lost following menopause. This loss of protection has been linked to the loss of estrogen and, in particular, to the loss of estrogen's ability to regulate the levels of serum lipids. The nature of estrogen's ability to regulate serum lipids is not well understood, but evidence indicates that estrogen can up-regulate the low density lipid (LDL) receptors in the liver which act to remove excess cholesterol. Additionally, estrogen appears to have some effect on the biosynthesis of cholesterol, and other beneficial effects on cardiovascular health. It has been reported in the literature that serum lipid levels in postmenopausal women having estrogen replacement therapy return to concentrations found in the premenopausal state.

At the present time, the most generally accepted method for treatment of disorders resulting in the postmenopausal state from the decline in estrogen levels is estrogen replacement therapy. The therapy may take the form of administering estrogen alone in so-called unopposed estrogen replacement therapy (ERT) or in the form of coadministering estrogen and progestin in a so-called hormonal replacement therapy (HRT) regimen. There are, however, major liabilities associated with chronic administration of estrogen in postmenopausal women having to do with adverse effects on reproductive tissues, namely breast and uterus. Women on ERT develop endometrial cancer at rates three to six times higher than nonusers after three to six years of use; after ten years of ERT, the risk ratio increases to tenfold. A growing body of literature suggests that long-term ERT (10–15 years) causes a thirty to fifty percent increase in the risk of breast cancer.

To combat these deleterious effect of ERT, the coadministration of progestin along with estrogen in a combined hormonal replacement therapy (HRT) is employed, since progestin acts to limit uterine stimulation and thus reduce the risk of uterine cancer.

Because of these known and suspected or feared liabilities of estrogen therapy, prescription of and patient compliance with chronic estrogen replacement therapy has been poor. It has been estimated that, in the United States among postmenopausal women for whom ERT or HRT has been prescribed, fewer than forty percent continue therapy beyond one year.

As a consequence, there is a need for the development of postmenopausal therapy agents which possess the ideal pharmacological profile: for example agents which produce the beneficial effects of estrogen upon vasomotor systems, skeletal tissue and the cardiovascular system without producing the adverse effects of estrogen upon reproductive tissues. Agents possessing such an estrogen profile would reverse the effects of estrogen deficiency in certain tissues while at the same time bypassing or failing to act in tissues in which estrogen produces adverse effects. The term selective estrogen receptor modulators or "SERMs" has been applied such compounds which possess this tissue selective profile. SERMs are defined as compounds producing estrogen agonism in one or more desired target tissues such as bone, liver, etc., together with estrogen antagonism and/or minimal (i. e. clinically insignificant) agonism in reproductive tissues such as the breast or uterus.

SUMMARY OF THE INVENTION

In accordance with the principle embodiment of the present invention, there is provided a class of substituted 1H-indene and 2,3-dihydro-1H-indene compounds having activity as selective estrogen receptor modulators of formula I:

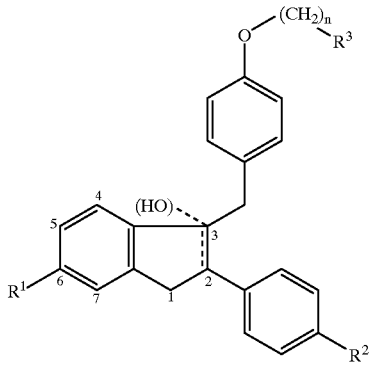

or a pharmaceutically acceptable salt thereof wherein $R^1$ is selected from the group consisting of —H. —OH, —O($C_1$–$C_4$ alkyl), —OCOAr, —OCO($C_1$–$C_6$ alkyl), and —OSO$_2$($C_2$–$C_6$ alkyl), where Ar is unsubstituted phenyl or phenyl substituted with one or more substituents selected from the group consisting of $C_1$–$C_4$ alkyl, $C_1$–$C_4$ alkoxy, halo and hydroxy.

The substituent $R^2$ is selected from the group consisting of —H, —OH, —O($C_1$–$C_4$ alkyl), —OCOAr, —OCO ($C_1$–$C_6$ alkyl), —OSO$_2$($C_2$–$C_6$ alkyl), and halo; $R^3$ is selected from the group consisting of 1-piperidinyl, 1-pyrrolidinyl, methyl-1-pyrrol-idinyl, dimethyl-1-pyrrolidinyl, 4-morpholino, dimethylamino, diethylamino, diisopropylamino, or 1-hexamethyleneimino; and n is 2 or 3.

The dotted line bond between the carbon atoms at positions 2 and 3 of the indene nucleus represent an optional double bond with the proviso that when the double bond is absent, the parenthetic hydroxy group at position 3 is present and vice versa.

In another embodiment, the present invention provides a compound useful as an intermediate in the preparation of compounds of formula I above selected from the group consisting compounds having the structural formulae II and III:

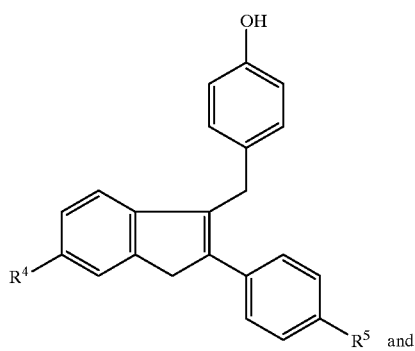

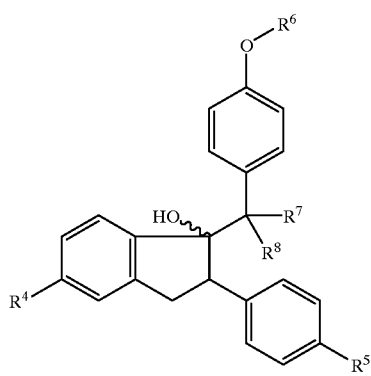

where $R^4$ and $R^5$ are protected hydroxy groups, $R^7$ and $R^8$ are both hydrogen or —$SR^{10}$ where $R^{10}$ is methyl or ethyl or $R^7$ and $R^8$, taken together with the carbon atom to which they are attached form a ring having the formula

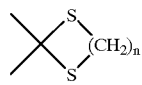

where n is 2 or 3.

$R^6$ is selected from the group consisting of hydrogen, benzyl, and —O($CH_2$)$_n R^3$ where $R^3$ is as defined above, with the proviso that when $R^6$ is hydrogen, $R^7$ and $R^8$ are also hydrogen.

The present invention further relates to pharmaceutical compositions comprising a compound of formula I, optionally containing estrogen or progestin, and the use of such compounds, alone, or in combination with estrogen or progestin, for treating osteoporosis and cardiovascular related pathological conditions, particularly hyperlipidemia.

DETAILED DESCRIPTION OF THE INVENTION

As will be recognized by those skilled in the art, certain compounds of the present invention contain one or more asymmetric or chiral centers. The present invention contemplates the individual enantiomers as well as the racemic modifications of the compounds described above. Specific enantiomers may be isolated, if desired, by techniques well known in the art such as the preparation of diastereomeric salts of the free base form with a resolved optically active acid followed by recrystallization and subsequent re-conversion to the free base or by separation on chiral chromatographic columns.

While the generic scope of compounds contemplated within the present invention is as defined above for structural formula I, specific examples of compounds falling within the scope of the present invention include:

6-hydroxy-2-phenyl-3-[(4-(2-pyrrolidin-1-yl-ethoxy)-phenyl)methyl]-1H-indene;
6-methoxy-2-phenyl)-3-[(4-(2-pyrrolidin-1-yl-ethoxy)-phenyl)methyl]-1H-indene;
6-hydroxy-2-(4-hydroxyphenyl)-3-[(4-(2-pyrrolidin-1-yl-ethoxy)phenyl)methyl]-1H-indene;
6-hydroxy-2-(4-methoxyphenyl)-3-[(4-(2-pyrrolidin-1-yl-ethoxy)phenyl)methyl]-1H-indene;
6-methoxy-2-(4-methoxyphenyl)-3-[(4-(2-pyrrolidin-1-yl-ethoxy)phenyl)methyl]-1H-indene;
6-hydroxy-2-(4-hydroxyphenyl)-3-[(4-(2-piperidin-1-yl-ethoxy)phenyl)methyl]-1H-indene;
6-hydroxy-2-(4-methoxyphenyl)-3-[(4-(2-piperidin-1-yl-ethoxy)phenyl)methyl]-1H-indene;
6-methoxy-2-(4-methoxyphenyl)-3-[(4-(2-piperidin-1-yl-ethoxy)phenyl)methyl]-1H-indene;
6-acetoxy-2-phenyl-3-[(4-(2-pyrrolidin-1-yl-ethoxy)-phenyl)-methyl]-1H-indene;
6-benzoyloxy-2-phenyl-3-[(4-(2-pyrrolidin-1-yl-ethoxy)-phenyl)methyl]indene;
6-methylsulfonyloxy-2-phenyl-3-[(4-(2-pyrrolidin-1-yl-ethoxy)phenyl)methyl]indene;
6-acetoxy-2-phenyl-3-[(4-(2-piperidin-1-yl-ethoxy)-phenyl)-methyl]-1H-indene;
6-benzoyloxy-2-phenyl-3-[(4-(2-piperidin-1-yl-ethoxy)-phenyl)methyl]-1H-indene;
6-methylsulfonyloxy-2-phenyl-3-[(4-(2-piperidin-1-yl-ethoxy)phenyl)methyl]-1H-indene;
6-hydroxy-2-(4-acetoxyphenyl)-3-[(4-(2-pyrrolidin-1-yl-ethoxy)phenyl)methyl]-1H-indene; 6-hydroxy-2-(4-benzoyloxyphenyl)-3-[(4-(2-pyrrolidin-1-yl-ethoxy)phenyl)methyl]-1H-indene;
6-hydroxy-2-(4-methylsulfonyloxyphenyl)-3-[(4-(2-pyrrolidin-1-yl-ethoxy)phenyl)methyl]-1H-indene;
6-hydroxy-2-(4-acetoxyphenyl)-3-[(4-(2-piperidin-1-yl-ethoxy)phenyl)methyl]-1H-indene;
6-hydroxy-2-(4-benzoyloxyphenyl)-3-[(4-(2-piperidin-1-yl-ethoxy)phenyl)methyl]-1H-indene; and
6-hydroxy-2-(4-methylsulfonyloxyphenyl)-3-[(4-(2-piperidin-1-yl-ethoxy)phenyl)methyl]-1H-indene.

Preferred compounds of the present invention are those in which $R^1$ and $R^2$ are independently selected from hydroxy and $C_1$–$C_4$ alkoxy, and n is 2.

Particularly preferred compounds of the present invention are compounds of structural formula I above in which $R^1$ and $R^2$ are independently selected from hydroxy and $C_1$–$C_4$ alkoxy (particularly methoxy), n is 2 and $R^3$ is 1-pyrrolidinyl or 1-piperidinyl.

Particularly preferred compounds of the present invention include:

6-hydroxy-2-(4-hydroxyphenyl)-3-[(4-(2-piperidin-1-yl-ethoxy)phenyl)methyl]-1H-indene;
6-hydroxy-2-(4-methoxyphenyl)-3-[(4-(2-piperidin-1-yl-ethoxy)phenyl)methyl]-1H-indene; and
6-methoxy-2-(4-methoxyphenyl)-3-[(4-(2-piperidin-1-yl-ethoxy)phenyl)methyl]-1H-indene.

Compounds as defined by the chemical structures II and III above are useful as intermediates in methods for the preparation of compounds of formula I of the present invention.

Specific examples of compounds falling within the scope of this aspect of the present invention include:

2,3-dihydro-3,6-dihydroxy-2-phenyl-3-[(4-(2-pyrrolidin-1-yl-ethoxy)phenyl)methyl]-1H-indene;
2,3-dihydro-3-hydroxy-6-methoxy-2-phenyl-3-[(4-(2-pyrrolidin-1-yl-ethoxy)phenyl)methyl]-1H-indene;
2,3-dihydro-3,6-dihydroxy-2-(4-hydroxyphenyl)-3-[(4-(2-pyrrolidin-1-yl-ethoxy)phenyl)methyl]-1H-indene;
2,3-dihydro-3,6-dihydroxy-2-(4-methoxyphenyl)-3-[(4-(2-pyrrolidin-1-yl-ethoxy)phenyl)methyl]-1H-indene;
2,3-dihydro-3,6-dihydroxy-2-(4-hydroxyphenyl)-3-[(4-(2-piperidin-1-yl-ethoxy)phenyl)methyl]-1H-indene;
2,3-dihydro-3,6-dihydroxy-2-(4-methoxyphenyl)-3-[(4-(2-piperidin-1-yl-ethoxy)phenyl)methyl]-1H-indene;
2,3-dihydro-3-hydroxy-6-acetoxy-2-phenyl-3-[(4-(2-pyrrolidin-1-yl-ethoxy)phenyl)methyl]-1H-indene;
2,3-dihydro-3-hydroxy-6-benzoyloxy-2-phenyl-3-[(4-(2-pyrrolidin-1-yl-ethoxy)phenyl)methyl]-1H-indene;
6-methylsulfonyloxy-2-phenyl-3-[(4-(2-pyrrolidin-1-yl-ethoxy)phenyl)methyl]-1H-indene;
6-acetoxy-2-phenyl-3-[(4-(2-piperidin-1-yl-ethoxy)-phenyl)methyl] - 1H-indene;
6-benzoyloxy-2-phenyl-3-[(4-(2-piperidin-1-yl-ethoxy)-phenyl)methyl]-1H-indene;
6-methylsulfonyloxy-2-phenyl-3-[(4-(2-piperidin-1-yl-ethoxy)phenyl)methyl]-1H-indene;
6-hydroxy-2-(4-acetoxyphenyl)-3-[(4-(2-pyrrolidin-1-yl-ethoxy)phenyl)methyl]-1H-indene;
6-hydroxy-2-(4-benzoyloxyphenyl)-3-[(4-(2-pyrrolidin-1-yl-ethoxy)phenyl)methyl]-1H-indene;
6-hydroxy-2-(4-methylsulfonyloxyphenyl)-3-[(4-(2-pyrrolidin-1-yl-ethoxy)phenyl)methyl]-1H-indene;
6-hydroxy-2-(4-acetoxyphenyl)-3-[(4-(2-piperidin-1-yl-ethoxy)phenyl)methyl]-1H-indene;
6-hydroxy-2-(4-benzoyloxyphenyl)-3-[(4-(2-piperidin-1-yl-ethoxy)phenyl)methyl]-1H-indene; and
6-hydroxy-2-(4-methylsulfonyloxyphenyl)-3-[(4-(2-piperidin-1-yl-ethoxy)phenyl)methyl]-1H-indene.

General terms used in the description of compounds herein described bear their usual meanings. For example, "$C_1$–$C_6$ alkyl" refers to a monovalent radical derived by the removal of a single hydrogen atom from a straight or branched aliphatic alkane of 1 to 6 carbon atoms including moieties such as methyl, ethyl, propyl, isopropyl, butyl, n-butyl, pentyl, isopentyl, hexyl, isohexyl, and the like.

Similarly, the term "$C_1$–$C_4$ alkoxy" represents a $C_1$–$C_4$ alkyl group, as defined above, attached to the parent molecular moiety through an oxygen atom and include moieties such as, for example, methoxy, ethoxy, n-propoxy, isopropoxy, and the like. Of these alkoxy groups, methoxy is particularly preferred.

The term "hydroxy protecting group" denotes a substituent of the type defined in Chapter 2, "Protection for the Hydroxyl Group . . . " in T. H. Greene, et al., "Protective Groups in Organic Synthesis," Second Edition, John Wiley & Sons, New York, 1991 and include groups such as unsubstituted and substituted methyl, ethyl and benzyl ether groups, and esters and sulfonates.

The term "protected hydroxy group" denotes a hydroxyl group, attached to the parent molecular moiety, protected by replacement of the hydroxy hydrogen atom with a protecting group as defined above.

As used herein, the term "estrogen" includes steroidal compounds having estrogenic activity such as, for example, 17β-estradiol, estrone, conjugated estrogen (Premarin®), equine estrogen, 17β-ethynyl estradiol, and the like. As used herein, the term "progestin" includes compounds having progestational activity such as, for example, progesterone, norethylnodrel, nongestrel, megestrol acetate, norethindrone, and the like.

The starting material for preparing compounds of the present invention is a compound of formula 1:

tective group as well as desulfurizes the dithiane moiety leaving the tertiary alcohol intact. The reductive transformations thereby give a benzylic indanol intermediate of formula 3, which, in turn, is dehydrated to a phenolic indene of formula II. This synthetic route is as shown below in Reaction Scheme I, where $R^4$ and $R^5$ are as defined above.

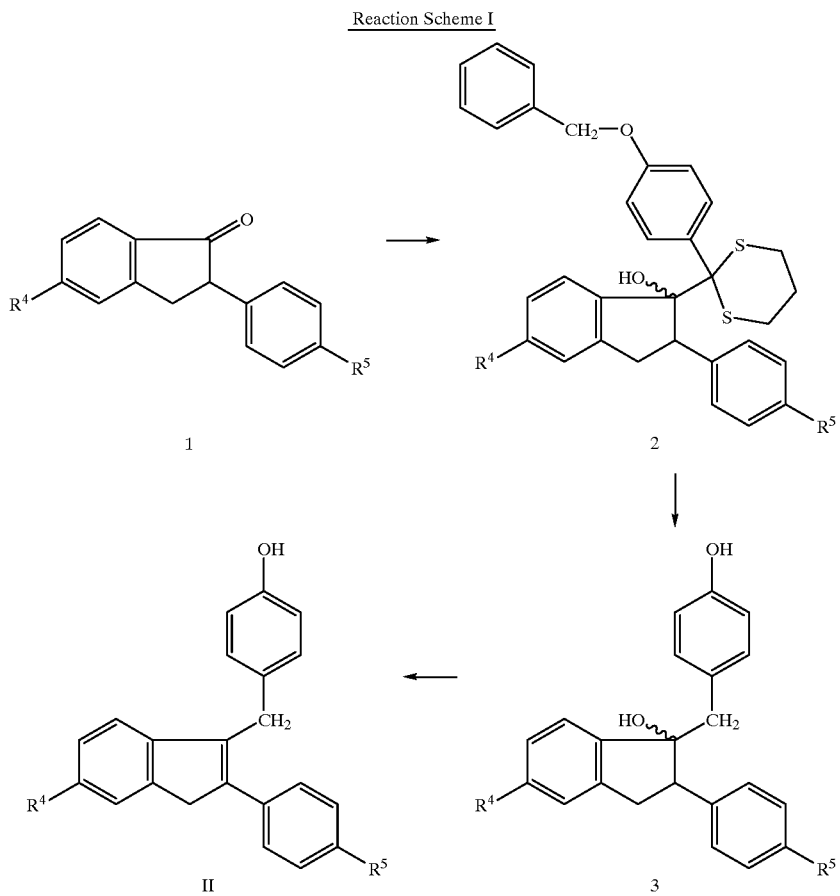

Reaction Scheme I

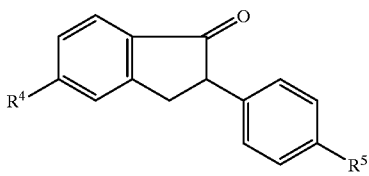

1 wherein $R^4$ is —H or —$OR^9$ in which $R^9$ is a hydroxy protecting group; and $R^5$ is —H, halo, or —$OR^9$. Compounds of formula 1 are well known in the art and are prepared essentially as described by Brown, D. W., Denman, C., and O'Donnell, H. J., in *J. Chem. Soc. C*, 19: 3195–3198 (1971), the disclosure of which is herein incorporated by reference.

In preparing compounds of the present invention, generally, a 1-indanone of formula 1 is alkylated with an organometallic reagent derived from a 1,3-dithianyl derivative of 4-benzyloxybenzaldehyde, to provide a carbinol intermediate of formula 2. The carbinol intermediate is then reduced with Raney nickel which removes the benzyl pro- In the first step of the process shown in Scheme I, an indanone compound of formula 1 is converted to the dithianyl derivative of an alpha-hydroxy ketone of formula 2 via a two-step protocol. Initially, a dithianyl derivative of an aromatic aldehyde is metalated to the corresponding anion. Appropriate dithiane derivatives for this reaction scheme are those which contain functional groups that are compatable with the strongly basic conditions which are required for the anion formation. The metalation is usually carried out by lithiation of the dithiane derivative with an alkyllithium reagent such as n-, s-, or t-butyl lithium; n-butyl lithium is preferred. The lithiation reaction is conducted in an inert solvent such as tetrahydrofuran, dioxane, or diethyl ether and under an inert atmosphere such as nitrogen or argon. To minimize side reactions and assure stability of the dithiane anion, once formed, a reduced temperature in the range of −78 to 0° C. is used. The preferred conditions for the reaction involve the use of tetrahydrofuran as solvent at a temperature of about −40° C.

The lithiated dithiane anion is not isolated, but upon completion of the lithiation reaction, is allowed to react with an indanone of structure 1 in an inert solvent. Although an excess of either the lithiated dithiane or the indanone can be used, it is preferred to use one equivalent of each so as to avoid wasting one of the components. The reaction is conducted in an inert solvent which is compatable with the reactive organometallic species present. For convenience it is advantageous to use the same solvent as that for the initial lithiation, tetrahydrofuran being preferred. Although the temperature employed in the addition step is not crucial, it is preferred to keep the temperature low (−78° C.) to minimize the formation of by-products. Under the preferred conditions, the addition reaction is over in about 1 to 3 hours. Similar lithiation reactions and addition reactions are described by L. F. Fieser and M. Fieser in "Reagents for Organic Synthesis", Vol 2, pp 182–4 (1969).

In the second step of Scheme I, the intermediate of formula 2 is desulfurized by reduction in an inert solvent with a hydrogenation catalyst. A nickel catalyst such as Raney nickel is preferred. Desulfurization reactions of this sort are well known to those skilled in the art and are carried out similarly to the reductions described in L. F. Fieser and M. Fieser in "Reagents for Organic Synthesis", Vol 1, p. 727–31 (1967). During the course of the desulfurization reaction, the benzyl ether protective group initially present in a formula 2 compound is also removed reductively. In order to increase the rate of the desulfurization and improve the yield of the reaction, it is preferable to use a large excess of the Raney nickel reducing agent. Suitable solvents include alcohols such as methanol, ethanol, and isopropyl alcohol, esters, such as ethyl acetate, or ethers, such as tetrahydrofuran. The addition of a basic additive such as ammonium hydroxide is advantageous because acid-catalyzed side reactions are avoided and extraction of the product from the catalyst is facilitated. The temperature for the desulfurization reaction is not critical, but should be sufficient to effect completion of the reaction in a reasonable period of time without encouraging the formation of undesirable by-products. A preferred temperature range for this reaction is from about 25° C. to about 60° C. Under the preferred conditions conditions for desulfurization (a 10-fold w/w excess of catalyst, ethanol solvent with ammonium hydroxide additive, an initial hydrogen pressure of 60 psi (413.7 kP) and a temperature of 25° C.) a formula 3 2,3-dihydro-1H-indene tertiary carbinol compound will be prepared via the preferred process in about 12 to about 24 hours.

In the final reaction shown in Scheme I, the tertiary carbinol formula 3 compound is dehydrated to form an indene compound of formula II, Such dehydrative reactions are well known to those skilled in the art and can be conducted under a wide range of acidic, basic, or neutral conditions. In the present case, the formula 3 compound is dehydrated under the influence of an acidic catalyst such as boric acid, hydrobromic acid, hydrochloric acid, naphthalene sulfonic acid, oxalic acid, methane sulfonic acid, toluene sulfonic acid, potassium bisulfate, and the like. Although less than one equivalent of the catalyst may be required to effect the dehydration at a satisfactory reaction rate, it is usually preferable to use between one and one hundred equivalents of the acid catalyst. The dehydration reaction is conducted in an inert solvent such as an alcohol, aromatic hydrocarbon, or an ether. For the present reaction, a preferred variation involves the use of a 100 fold molar excess of 5 normal HCl in ethanol at a temperature of 25° C. Under these preferred conditions, the dehydration reaction is complete after about 0.5 to 2 hours.

Compounds of formula II are useful for the preparation of pharmaceutically active compounds of formula I of the present invention. To prepare a compound of formula I, a formula II compound is reacted with a compound of formula 4:

$$R^3—(CH_2)_n—Q \qquad 4$$

in which $R^3$ and n are as defined above and Q is bromo or, preferably, chloro, to form a compound of formula Ia. The formula Ia compound is then deprotected, when $R^5$ and/or $R^6$ hydroxy protecting groups are present, to form a compound of formula Ib. These process steps are shown in Reaction Scheme II below.

Reaction Scheme II

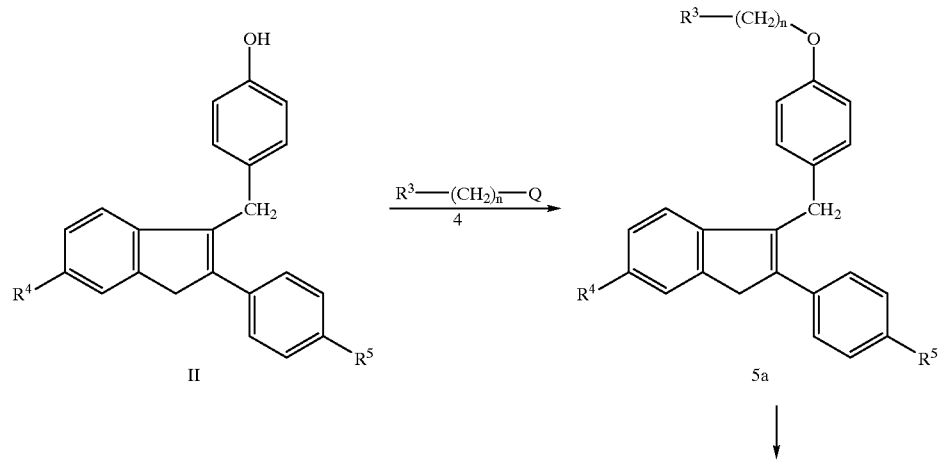

-continued

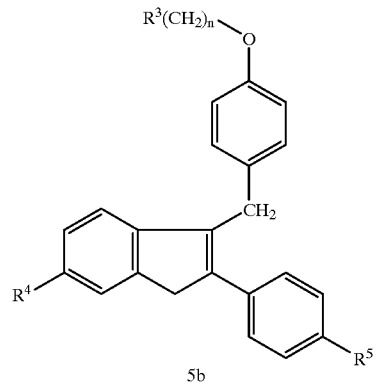

5a: $R^4$, $R^5$, $R^3$, and $n$ are as defined above;
5b: $R^4$ = H or OH,
$R^5$ = H, OH or halo
$R^3$ and $n$ are as defined above.

In the first step of the process shown in Scheme II, the alkylation is carried out via standard procedures. Compounds of formula 4 are commercially available or are prepared by means well known to one of ordinary skill in the art. Preferably, the hydrochloride salt of a formula 4 compound, particularly 2-chloroethylpiperidine hydrochloride, is used.

Generally, at least about 1 equivalent of a compound of formula II is reacted with 2 equivalents of a compound of formula 4 in the presence of at least about 4 equivalents of an alkali metal carbonate, preferably cesium carbonate or potassium carbonate, and an appropriate solvent.

Solvents for this reaction are those solvents or mixture of solvents which remain inert throughout the reaction. N,N-dimethylformamide, especially the anhydrous form thereof, is preferred.

The temperature employed in this step should be sufficient to effect completion of this alkylation reaction. Often, ambient temperature is sufficient and preferred, but in certain cases, higher temperatures may be required.

The present reaction preferably is run under an inert atmosphere, particularly nitrogen.

Under the preferred reaction conditions, this reaction will run to completion in about 16 to about 20 hours. Of course, the progress of the reaction can be monitored via standard chromatographic techniques.

As an alternative for preparing compounds of formula Ia, a formula II compound is reacted with an excess of an alkylating agent of formula 6

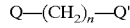        6 wherein Q and Q' each are the same or different leaving group, in an alkali solution. Appropriate leaving groups include sulfonates such as methanesulfonate, 4-bromobenzenesulfonate, toluenesulfonate, ethanesulfonate, isopropylsulfonate, 4-methoxybenzenesulfonate, 4-nitrobenzenesulfonate, 2-chlorobenzenesulfonate, triflate, and the like, halogens such as bromo, chloro, and iodo, and other related leaving groups. Halogens are preferred leaving groups and bromo is especially preferred.

A preferred alkali solution for this alkylation reaction contains potassium carbonate in an inert solvent such as, for example, methyethyl ketone (MEK) or dimethylformamide (DMF). In this solution, the 4-hydroxy group of the benzyl moiety of a formula II compound exists as a phenoxide ion which displaces one of the leaving groups of the alkylating agent.

This reaction proceeds best when the alkali solution containing the reactants and reagents is brought to reflux and allowed to run to completion. When using MEK as the preferred solvent, reaction times run from about 6 hours to about 20 hours.

The reaction product from this step is then reacted with 1-piperidine, 1-pyrrolidine, methyl-1-pyrrolidine, dimethyl-1-pyrrolidine, 4-morpholine, dimethylamine, diethylamine, or 1-hexamethyleneimine, or other secondary amines, via standard techniques, to form compounds of formula 5a. Preferably, the hydrochloride salt of piperidine is reacted with the alkylated intermediate from a formula II compound in an inert solvent, such as anhydrous DMF, and heated to a temperature in the range from about 60° C. to about 110° C. When the mixture is heated to a preferred temperature of about 90° C., the reaction only takes about 30 minutes to about 1 hour, however changes in the reaction conditions will influence the amount of time this reaction needs to be run to completion. The progress of this reaction step can be monitored via standard chromatographic techniques.

An alternative route for preparing compounds of the present invention is depicted in Reaction Scheme III, in which $R^3$, $R^4$ and $R^5$ are as defined above.

Reaction Scheme III

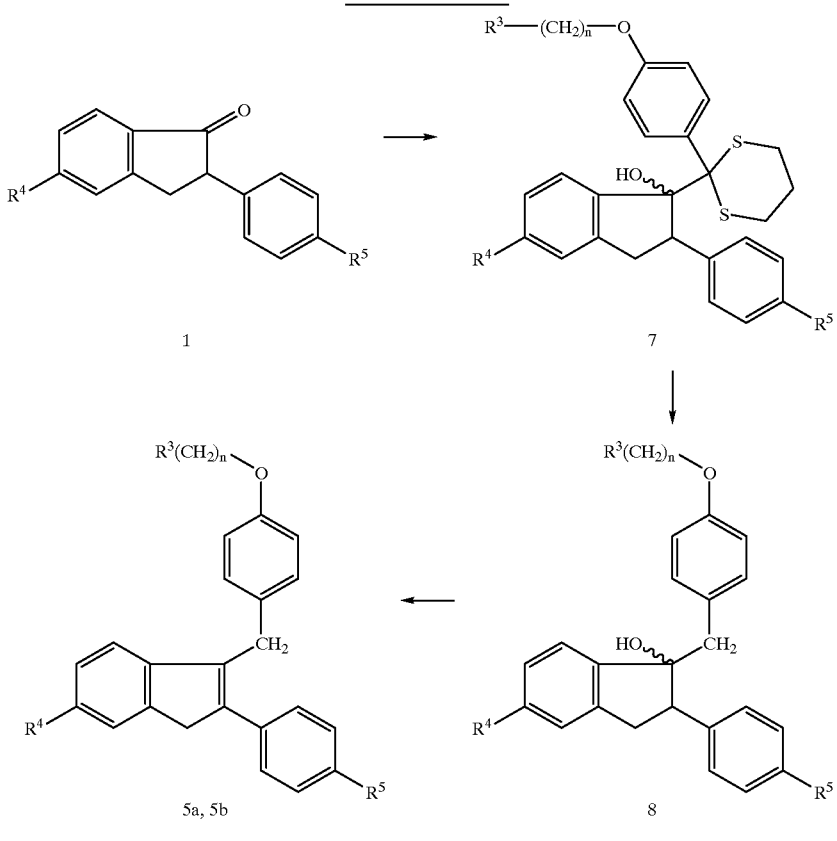

In the alternative synthetic sequence depicted in Reaction Scheme III, the starting material 1-indanone, 1, is reacted with a lithiodithiane anion. In this case, however, the precursor dithiane is derived from a 4-(di-N-substituted aminoalkoxy)benzaldehyde, thus installing the basic side chain moiety at an early stage of the synthesis. The product of the dithiane alkylation is a tertiary carbinol intermediate of formula 7. Raney nickel desulfurization to remove the dithiane gives rise to the intermediate of formula 8 and subsequent dehydration provides an indene derivative of formula 5.

The detailed reaction conditions and scope for the transformations in Reaction Scheme III are essentially the same as those for the analogous steps in Reaction Scheme I. However, care is taken to allow for a full equivalent of acid catalyst in the dehydrative final step, since the first equivalent will be consumed by the tertiary amine moiety present in the basic side chain.

Preferred compounds of formula I are obtained by cleaving, when $R^4$ and $R^5$ are protected hydroxy groups, the $R^9$ protecting groups of compounds formula II or III compounds via well known procedures. Numerous reactions for the formation and removal of such protecting groups are described in a number of standard works including, for example, T. Greene, et al., "Protective Groups in Organic Chemistry", Second Edition, John Wiley & Sons, New York, 1991. and "The Peptides", Vol. I, Schrooder and Lubke, Academic Press (London and New York, 1965). Methods for removing preferred $R^4$ and/or $R^5$ hydroxy protecting groups, particularly methyl, are essentially as described in Example 8, infra.

Other preferred compounds of formula I are prepared by replacing the 5- and/or 4'-position hydroxy moieties, when present, with a moiety of the formula —OCO($C_1$–$C_6$ alkyl), or —$SO_2$($C_2$–$C_6$ alkyl) via well known procedures; see, for example U.S. Pat. No. 4,358,593.

For example, when an —OCO($C_1$–$C_6$ alkyl) group is desired, a compound of formula I where $R^4$ and $R^5$ are both or are individually hydroxy is reacted with an acylating agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, e.g., Haslam, et al., *Tetrahedron*, 36:2409–2433 (1980).

The present reactions are carried out at moderate temperatures, in the range from about −25° C. to about 10° C., frequently under an inert atmosphere such as nitrogen gas. However, ambient temperature is usually adequate for the reaction to proceed.

Acylation of a 5-position and/or 4'-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

The aforementioned $R^1$ and/or $R^2$ groups of formula I compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, e.g., *Bull. Chem. Soc. Japan*, 38:1979 (1965), and *Chem. Ber.*, 788 and 2024 (1970).

Each of the above techniques which provide —OCO ($C_1$–$C_6$ alkyl) moieties are carried out in solvents as discussed above. Those techniques which do not produce an acid product in the course of the reaction, do not call for the use of an acid scavenger in the reaction mixture.

When a formula I compound is desired in which the 5- and/or 4'-position hydroxy group of a formula I compound is converted to a group of the formula —$OSO_2$($C_2$–$C_6$ alkyl), the mono- or dihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The dihydroxy compound also can be reacted with the appropriate sulfonic anhydride or mixed sulfonic anhydrides. Such reactions are carried out under conditions such as were explained above in the discussion of reaction with acid halides and the like.

Although the free-base form of formula I compounds can be used in the medical methods of treatment of the present invention, it is preferred to prepare and use a pharmaceutically acceptable salt form. The compounds used in the methods of this invention primarily form pharmaceutically acceptable acid addition salts with a wide variety of organic and inorganic acids. Such salts are also contemplated as falling within the scope of the present invention.

The term "pharmaceutically acceptable salts" as used throughout this specification and the appended claims denotes salts of the types disclosed in the article by Berge, et al., *J. Pharmaceutical Sciences*, 66(1): 1–19 (1977). Suitable pharmaceutically acceptable salts include salts formed by typical inorganic acids such as hydrochloric, hydrobromic, hydroiodic, nitric, sulfuric, phosphoric, hypophosphoric, and the like, as well as salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids. Such pharmaceutically acceptable organic acid addition salts include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluene-sulfonate, xylenesulfonate, tartarate, and the like. Preferred salts are the hydrochloride and oxalate salts.

The pharmaceutically acceptable acid addition salts are typically formed by reacting a compound of formula I with an equimolar or slight molar excess of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

Test Procedures

Illustrating methods of utilizing the compounds of the present invention, a postmenopausal model was used in which effects of different treatments upon circulating lipids were determined.

Seventy-five day old female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room is 12 hours light and 12 hours dark.

Dosing Regimen Tissue Collection. After a one week acclimation period (therefore, two weeks post-OVX) daily dosing with test compound is initiated. 17 -ethynyl estradiol ("EE2" obtained from Sigma Chemical Co., St. Louis, Mo.) or the test compound are given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine: xylazine (2:1, V:V) mixture and a blood sample is collected by cardiac puncture. The animals are then sacrificed by asphyxiation with $CO_2$, the uterus is removed through a midline incision, and a wet uterine weight is determined.

Cholesterol Analysis. Blood samples are allowed to clot at ambient temperature for 2 hours, and serum is obtained following centrifugation for 10 minutes at 3000 rpm. Serum cholesterol is determined using a Boehringer Mannheim Diagnostics high performance cholesterol assay. Briefly, the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotometrically at 500 nm. Cholesterol concentration is then calculated against a standard curve Uterine Eosinophil Peroxidase (EPO) Assay. Uteri are kept at 4° C. until time of enzymatic analysis. The uteri are then homogenized in 50 volumes of 50 mM Tris buffer (pH-8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosonophils in the uterus is an indication of estrogenic activity of a compound. The maximal velocity of a 15 second interval is determined over the initial, linear portion of the reaction curve.

The result of these tests with representative compounds of the present invention, administered at three different dose levels, are given in Tables 1a, 1b and 1c in comparison with 17 -ethynyl estradiol (EE2). The various data table represent tests conducted using the protocols described immediately above, but on different days. In each case however there is a comparison of the compounds tested with 17-ethynyl estradiol (EE2).

TABLE 1a

| Compound | Dose (mg/kg) | Increase in Uterine Weight (%)[b] | Serum Eosinophil ($V_{max}$)[c] | Decrease in Cholesterol (%)[d] |
|---|---|---|---|---|
| EE2[a] | 0.1 | 108.4* | 31.5 | 92.4* |
| Example 3 | 0.1 | −0.7 | 1.2 | 1.5 |
|  | 1 | 6.4 | 0.0 | −13.2 |
|  | 10 | 11.4 | 2.1 | −0.2 |
| Example 4 | 0.1 | −1 | 3.0 | −11 |
|  | 1 | 8.5 | 0.9 | 7.3 |
|  | 10 | 94.6* | 39.0 | 57.6* |

TABLE 1b

| Compound | Dose (mg/kg) | Increase in Uterine Weight (%)[b] | Serum Eosinophil ($V_{max}$)[c] | Decrease in Cholesterol (%)[d] |
|---|---|---|---|---|
| EE2[d] | 0.1 | 82.5* | 109.2 | 87.8 |
| Example 5 | 0.1 | 27.0* | 8.4 | 35.2* |
|  | 1 | 42.0* | 21.3 | 64.0* |
|  | 10 | 28.8* | 33.3 | 70.8* |
| Example 6 | 0.1 | 60.1* | 19.2 | 64.5* |
|  | 1 | 19.1 | 4.8 | 58.0 |
|  | 10 | 15.7 | 4.2 | 62.4 |

TABLE 1c

| Compound | Dose (mg/kg) | Increase in Uterine Weight (%)[b] | Serum Eosinophil ($V_{max}$)[c] | Decrease in Cholesterol (%)[d] |
|---|---|---|---|---|
| EE2[a] | 0.1 | 133.3* | 136.2* | 76.1* |
| Example 8 | 0.1 | 60.1* | 19.2 | 64.5* |
|  | 1 | 19.1 | 4.8 | 58.0 |
|  | 10 | 15.7 | 4.2 | 62.4 |

[a]17-α-Ethynyl estradiol
[b]Uterine Weight % increase versus the ovarierectomized controls
[c]Eosinophil peroxidase $V_{maxium}$
[d]Serum cholesterol decrease versus ovariectomized controls
*p < 0.05

The data in Tables 1a, 1b and 1c show that representative compounds in accordance with the present invention, when compared with 17-ethynyl estradiol (EE2), exhibit slective estrogen receptor modulating (SERM) activity; that is, they act like estrogens in certain tissues (e.g. reducing serum cholesterol levels) without exhibiting the underisrable effects of an estrogens in other tissues (e.g. inducing uterine weight gain).

Osteoporosis Test Procedure

Following the General Preparation Procedure, infra, rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the present invention and ethynyl estradiol ($EE_2$) in 20% hydroxypropyl β-cyclodextrin are orally administered to test animals.

Antagonist activity. Female, virus-antibody free, Sprague Dawley rats (21 days old) were obtained from Charles Rivers Labs (Portage, MI) and maintained as described above. Animals were given oral gavages of ethynyl estradiol at a dose of 0.1 mg/kg. which were followed by test compound in 20% beta-hydrocycyclodextrin), gavaged orally over adose range of 0.1 to 10 mg/kg. Daily gavages were continued for 3 days, after which the animals were sacrificed and uterine weight determined.

MCF-7 Proliferation Assay

MCF-7 breast adenocarcinoma cells (ATCC HTB 22) are maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells are switched to maintenance medium supplemented with 10% dextran coated charcoal stripped fetal bovine serum (DCC-FBS) assay medium) in place of 10% FBS to deplete internal stores of steroids. MCF-7 cells are removed from maintenance flasks using cell dissociation medium ($Ca^{++}/Mg^{++}$ free HBSS (phenol red-free) supplemented with 10 mM HEPES and 2 mM EDTA). Cells are washed twice with assay medium and adjusted to 80,000 cells/mL. Approximately 100 mL (8,000 cells) are added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control are prepared in assay medium and 50 mL transferred to triplicate microcultures followed by 50 mL assay medium for a final volume of 200 mL. After an additional 48 hours at 37° C. in a 5% $CO_2$ humidified incubator, microcultures are pulsed with tritiated thymidine (1 mCi/well) for 4 hours. Cultures are terminated by freezing at −70° C. for 24 hours followed by thawing and harvesting of microcultures using a Skatron Semiautomatic Cell Harvester. Samples are counted by liquid scintillation using a Wallac BetaPlace β counter. Activity of a compound of formula I in the present assay demonstrates that the compound is of potential for treating hormonally-dependent cancer, particularly breast cancer.

DMBA-Induced Mammary Tumor Inhibition

Estrogen-dependent mammary tumors are produced in female Sprague-Dawley rats which are purchased from Harlan Industries, Indianapolis, Indiana. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered one daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

Pharmaceutical Formulations

The present invention also provides pharmaceutical compositions which comprise one or more compounds of the present invention, formulated either alone or in combination with estrogen or progestinc with one or more non-toxic pharmaceutically acceptable carriers and/or excipients.

Pharmaceutical formulations of the present invention are prepared by procedures known in the art using well known and readily available ingredients. For example, the compounds of Formula I, either alone, or in combination with an estrogen or progestin compound, are formulated with common excipients, diluents, or carriers, and formed into tablets, capsules, suspensions, solutions, injectables, aerosols, powders, and the like.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

The formulations may be specially formulated for oral administration, in solid or liquid form, for parenteral injection, topical or aerosol administration, or for rectal or vaginal administration by means of a suppository.

The pharmaceutical compositions of this invention can be administered to humans and other mammals orally, rectally, intravaginally, parenterally, topically (by means of powders, ointments, creams, or drops), bucally or sublingually, or as an oral or nasal spray. The term "parenteral administration" refers herein to modes of administration which include intravenous, intramuscular, intraperitoneal, instrasternal, subcutaneous, or intraarticular injection or infusion.

Pharmaceutical compositions of this invention for parenteral administration comprise sterile aqueous or non-aqueous solutions, dispersions, suspensions, or emulsions, as well as sterile powders which are reconstituted immediately prior to use into sterile solutions or suspensions. Examples of suitable sterile aqueous and non-aqueous carriers, diluents, solvents or vehicles include water, physiological saline solution, ethanol, polyols (such as glycerol, propylene glycol, poly(ethylene glycol), and the like), and suitable mixtures thereof, vegetable oils (such as olive oil), and injectable organic esters such as ethyl oleate. Proper fluidity is maintained, for example, by the use of coating materials such as lecithin, by the maintenance of proper particle size in the case of dispersions and suspensions, and by the use of surfactants.

Parenteral compositions may also contain adjuvants such as preservatives, wetting agents, emulsifying agents, and dispersing agents. Prevention of the action of microorganisms is ensured by the inclusion of antibacterial and antifungal agents, for example, paraben, chlorobutanol, phenol sorbic acid, and the like. It may also be desirable to include isotonic agents such as sugars, sodium chloride, and the like. Prolonged absorption of injectable formulations may be brought about by the inclusion of agents which delay absorption such as aluminum monostearate and gelatin.

In some cases, in order to prolong the effect of the drug, it is desirable to slow the absorption of the drug following subcutaneous or intramuscular injection. This may be accomplished by the use of a liquid suspension or crystalline or amorphous material of low water solubility or by dissolving or suspending the drug in an oil vehicle. In the case of the subcutaneous or intramuscular injection of a suspension containing a form of the drug with low water solubility, the rate of absorption of the drug depends upon its rate of dissolution.

Injectable "depot" formulations of the compounds of this invention are made by forming microencapsulated matrices of the drug in biodegradable polymers such as poly(lactic acid), poly(glycolic acid), copolymers of lactic and glycolic acid, poly (orthoesters), and poly (anhydrides) these materials which are described in the art. Depending upon the ratio of drug to polymer and the characteristics of the particular polymer employed, the rate of drug release can be controlled.

Injectable formulations are sterilized, for example, by filtration through bacterial-retaining filters, or by presterilization of the components of the mixture prior to their admixture, either at the time of manufacture or just prior to administration (as in the example of a dual chamber syringe package).

Solid dosage forms for oral administration include capsules, tablets, pills, powders, and granules. In such solid dosage forms, the active component is mixed with at least one inert, pharmaceutically acceptable carrier such as sodium citrate, or dicalcium phosphate, and/or (a) fillers or extenders such as starches, lactose, glucose, mannitol, and silicic acid, (b) binding agents such as carboxymethyl-cellulose, alginates, gelatin, poly(vinylpyrrolidine), sucrose and acacia, (c) humectants such as glycerol, (d) disintegrating agents such as agar-agar, calcium carbonate, potato or tapioca starch, alginic acid, silicates and sodium carbonate, (e) solution retarding agents such as paraffin, (f) absorption accelerating agents such as quaternary ammonium compounds, (g) wetting agents such as cetyl alcohol and glycerin monostearate, (h) absorbents such as kaolin and bentonite clay, and (i) lubricants such as talc, calcium stearate, magnesium stearate, solid poly(ethylene glycols), sodium lauryl sulfate, and mixtures thereof. In the case of capsules, tablets and pills, the dosage form may also contain buffering agents.

Solid compositions of a similar type may also comprise the fill in soft or hard gelatin capsules using excipients such as lactose as well as high molecular weight poly(ethylene glycols) and the like.

Solid dosage forms such as tablets, dragees, capsules, pills and granules can also be prepared with coatings or shells such as enteric coatings or other coatings well known in the pharmaceutical formulating art. The coatings may contain opacifying agents or agents which release the active ingredient(s) in a particular part of the digestive tract, as for example, acid soluble coatings for release of the active ingredient(s) in the stomach, or base soluble coatings for release of the active ingredient(s) in the intestinal tract.

The active ingredient(s) may also be microencapsulated in a sustained-release coating, with the microcapsules being made part of a pill of capsule formulation.

Liquid dosage forms for oral administration of the compounds of this invention include solution, emulsions, suspensions, syrups and elixirs. In addition to the active components, liquid formulations may include inert diluents commonly used in the art such as water or other pharmaceutically acceptable solvents, solubilizing agents and emulsifiers such as ethanol, isopropanol, ethyl carbonate, ethyl acetate, benzyl alcohol, benzyl benzoate, propylene glycol, 1,3-butylene glycol, dimethyl formamide, oils (in particular, cottonseed, ground nut, corn, germ, olive, castor, and sesame oils), glycerol, tetrahydrofurfuryl alcohol, poly(ethylene glycols), fatty acid esters of sorbitol, and mixtures thereof.

Besides inert diluents, the liquid oral formulations may also include adjuvants such as wetting agents, emulsifying and suspending agents, and sweetening, flavoring, and perfuming agents.

Liquid suspension, in addition to the active ingredient(s) may contain suspending agents such as ethoxylated isostearyl alcohols, polyoxyethylene sorbitol and sorbitan esters, microcrystalline cellulose, aluminum metahydroxide, bentonite clay, agar-agar, and tragacanth, and mixtures thereof.

Compositions for rectal or intravaginal administration are prepared by mixing one or more compounds of the present invention with suitable non-irritating excipients such as cocoa butter, polyethylene glycol or any suppository wax which is a solid at room temperature, but liquid at body temperature and therefore melt in the rectum or vaginal cavity to release the active component(s). The compounds are dissolved in the melted wax, formed into the desired shape, and allowed to harden into the finished suppository formulation.

Compounds of the present invention may also be administered in the form of liposomes. As is know in the art, liposomes are generally derived from phospholipids or other lipid substances. Lipososome formulations are formed by mono- or multilamellar hydrated liquid crystals which are dispersed in an aqueous medium. Any non-toxic, pharmaceutically acceptable, and metabolizable lipid capable of forming liposomes can be used. The present compositions in liposome form can contain, in addition to one or more active compounds of the present invention, stabilizers, excipients, preservatives, and the like. The preferred lipids are phospholipids and the phosphatidyl cholines (lecithins), both natural and synthetic.

Methods for forming liposomes are know in the art as described, for example, in Prescott, Ed., *Methods in Cell Biology*, Volume XIV, Academic Press, New York, N.Y. (1976), p. 33 et seq.

Dosage forms for topical administration of the compounds of the present invention include powders, sprays, ointments, creams, and inhalants. The active ingredient(s) is mixed under sterile conditions with a suitable pharmaceutically acceptable carrier and preservatives, buffers, or propellants as needed. Opthalmic formulations, eye ointments, and solutions are also contemplated as falling within the scope of the present invention.

The present invention also provides methods for alleviating pathological postmenopausal conditions in women, particularly osteoporosis and hyperlipidemia, which comprise administering an effective amount of a compound of Formula I, either alone, or in combination with a therapeutically effective amount of estrogen or progestin.

In the case of combined administration of a compound of the present invention in conjunction with estrogen or progestin for the treatment of osteoporosis or hyperlipidemia, the patient receives the benefits of each pharmaceutical agent while the compounds of the present invention inhibit undesirable side-effects of estrogen or progestin.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin®, and norethylnodrel and norethindrone are preferred progestin-based agents.

As used herein, the term "effective amount" or "therapuetically effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

A typical daily dose will contain a nontoxic dosage level of from about 5 mg to about 600 mg/day of a compound of the present invention. Preferred daily doses generally are from about 15 mg to about 80 mg/day. Actual dosage levels of compounds of the present invention are varied so as to administer an amount of the compound which is effective to bring about the desired therapeutic affect. The dose required for a given patient will vary depending upon the severity of the condition being treated, the age, weight, and sex and general state of health of the patient. However, it is within the skill of the practitioner of the medical art to "dose titrate" the patient; that is, to begin administering a dose known to be below the amount required to bring about the desired therapeutic effect and to gradually increase the dose until the desired effect is achieved.

The following examples are presented to further illustrate the preparation of compounds and formulations of the present invention. It is not intended that the invention be limited in scope by reason of any of the following examples.

NMR data for the following Examples were generated on a GE 300 MHz NMR instrument, and anhydrous $d_6$-dimethyl-sulfoxide ($d_6$-DMSO) was used as the solvent unless otherwise indicated.

Preparation 1

Preparation of 4-[2-(1-piperdinyl)ethoxy]benzaldehyde,

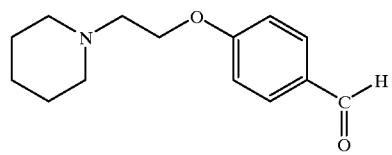

A 1 L 3-neck round bottom flask was charged with anhydrous THF (200 mL), 1-piperidinylethanol (14.9 g, 15.27 mL, 0.115 mol), 4-hydroxybenzaldehyde (14.16 g, 0.116 mol), and triphenylphosphine (31,21 g, 0.119 mol) under a nitrogen atmosphere. The above mixture was stirred and diethylazodicarboxylate (DEAD; 22.6 g, 20.4 mL, 0.130 mol) in anhydrous THF (25 mL) was added dropwise over 15 min during which time the temperature was carefully monitored and not allowed to exceed 60° C. The reaction was stirred overnight at ambient temperature and then worked up by the addition of 10 mL 30% hydrogen peroxide and extraction of by ethyl ether. The organic layer was washed eight times with water, dried over anhydrous sodium sulfate, and concentrated to an oil. The oil was purified by chromatography over silica gel using a Waters LC2000 instrument. The elution solvent employed a gradient system beginning with 100% methylene chloride and ramping to 9:1 methylene chloride:methanol over 50 min at a flow rate of 150 mL/min. Concentration of appropriate fractions provided 9.2 g (35%) of the desired product as a pale brown oil.

$^1$H NMR (CDCl$_3$): δ 8.80 (s, 1H), 7.83 (d, J=8.0 Hz, 2H), 7.03 (d, J=8.0 Hz, 2H), 4.19 (t, J=7.0 Hz, 2H), 2.80 (t, J=7.0 Hz, 2H), 2.59–2.42 (m, 4H), 1.64–1.58 (m, 4H), 1.50–1.40 (m, 2H); MS (FD): m/e 223 (M+) $C_{14}H_{19}NO_2$.

Preparation 2

Preparation of 2-[4-[2-(1-piperdinyl)ethoxy]phenyl] 1,3-dithiane]

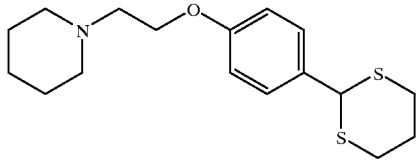

A 500 mL, 3-neck round bottom flask was charged with 4-[2-(1-piperdinyl)ethoxy]benzaldehyde (2.3 g, 10.0 mmol) and 1,3-propanedithiol (1.2 mL, 1.1 g, 10.2 mmol) in 250 mL of anhydrous chloroform under a nitrogen atmosphere. The solution was cooled to near 0° C. and dry HBr gas was slowly bubbled through the reaction mixture for 8 minutes. The mixture was allowed to warm to ambient temperature while stirring during 3.5 hr. The reaction mixture was then added to a large excess of 1N NaOH and ice and the chloroform layer was separated. The chloroform solution was washed with two 50 mL portions of 1N NaOH solution and two 25 mL portions of brine and dried over anhydrous sodium sulfate. After filtration and removal of the chloroform solvent, the residue was triturated with 1:1 hexane-:ethyl ether to provide 2.19 g (68%) of a crystalline product which was used without further purification.

$^1$H NMR: (CDCl$_3$): δ 7.39 (d, J=8.0 Hz, 2H), 6.83 (d, J=8.0 Hz, 2H), 5.13 (s, 1H), 4.10 (m, 1H), 3.13–2.78 (m, 6H), 2.58–2.48 (m, 4H), 2.20–2.10 (m, 1H), 2.00–1.83 (m, 1H), 1.63–1.58 (m, 4H), 1.43–1.40 (m, 2H); MS (FD): m/e 323 (M+); Anal.: Calc'd. for $C_{17}H_{25}NOS_2$: C, 63.11; H, 7.79; N, 4.33; Found: C, 63.10; H, 7.82; N, 4.35.

EXAMPLE 1

Preparation of 2-[4-(phenylmethoxy)phenyl]-2-[1-hydroxy-2-(4-methoxyphenyl)-5-methoxy]indanyl]-1,3-dithiane

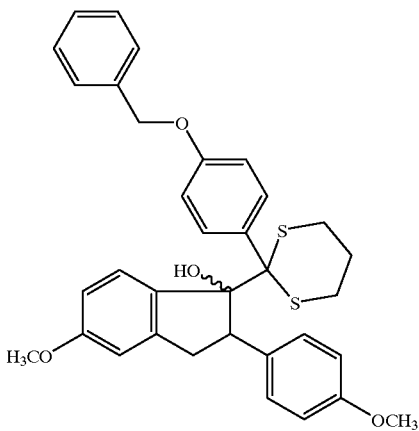

To a 500 mL 3 neck flame-dried round bottom flask under a nitrogen atmosphere was added 150 mL of anhydrous tetrahydrofuran and 2-[4-(phenylmethoxy)phenyl]1,3-dithiane], (4.76 g, 15.75 mmol), made in accordance with the method of F. Braucher, et al., Arch. Pharm., 328(3): 235–8 (1995). The resulting solution was cooled to −40° C. in an acetonitrile/dry ice bath and held at that temperature during the dropwise addition of n-butyl lithium (1.6 M, 10.5 mL, 15.75 mmol) in hexane. The resulting solution of lithiated dithiane was kept cold and stirred for an additional 20 minutes. Then a solution of 2-(4-methoxyphenyl)-5-methoxy-1-indanone (4.20 g, 15.75 mmol) in 75 mL of anhydrous THF was added dropwise over 20 minutes. The resulting reaction mixture was still kept at −40° C. while it was stirred for 2.5 hr longer. Then the reaction was worked up by cautious addition of 100 mL of iced 1N HCl solution followed by evaporation of most of the THF and extraction of the aqueous residue with ethyl acetate. The ethyl acetate layer was separated and washed with water. Then it was dried over anhydrous magnesium sulfate and evaporated to an oil. The oil was purified using silica gel chromatography (Waters Prep 2000) and an elution gradient from toluene to 9:1 toluene:ethyl acetate. Following concentration of the appropriate fractions, the desired product was isolated as 4.0 g (45%) of an amorphous solid.

$^1$H NMR (CDCl$_3$): δ 7.60 (s, 2H), 7.40–7.10 (m, 6H), 6.97 (d, J=7.0 Hz, 2H), 6.80 (d, J=8.0 Hz, 2H), 6.70 (d, J=7.0 Hz, 3H), 6.58 (s, 1H), 5.10 (s, 2H), 4.39 (s, 1H), 3.83 (s, 3H), 3.70 (s, 3H), 2.90–2.20 (m, 8H), 1.90 (m, 2H); MS (FD): m/e 554 (dehydrates); Anal.: Calc'd. for $C_{34}H_{34}O_4S_2$ with 1/3 mole toluene: C, 72.45; H, 6.13; Found: C, 72.97; H, 6.20.

EXAMPLE 2

Preparation of [4-hydroxyphenyl] [1-hydroxy-2-(4-methoxy-phenyl)-5-methoxy]indanyl]methane,

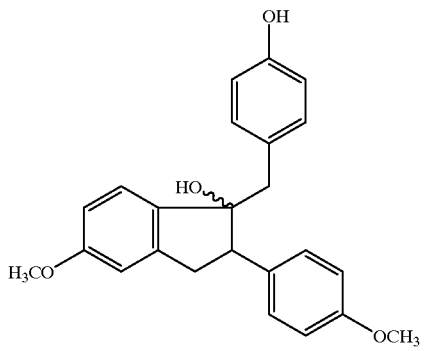

2-[Phenyl]-2-[1-hydroxy-2-(4-methoxyphenyl)-5-methoxy]indanyl]-1,3-dithiane (1.0 g), prepared by the method described above in Example 1, was dissolved in 75 mL absolute ethanol and 5 mL of 15M ammonium hydroxide. The solution was treated with 10 grams of Raney nickel, placed at an initial pressure of 60 psi under an atmosphere of hydrogen, and shaken overnight. The reaction mixture was then filtered through a pad of 1:1 talc and celite. Concentration of the filtrate provided an amorphous residue which was purified by radial chromatography over silica gel using 7:3 hexane:ethyl acetate to elute the desired product which was obtained as a white amorphous solid.

$^1$H NMR (CDCl$_3$): δ 7.03 (d, J=8.0 Hz, 1H), 6.95 (d, J=7.0 Hz, 4H), 6.77 (d, J=8.0 Hz, 4H), 6.65 (d, J=7.0 Hz, 2H), 4.73 (s, 1H), 3.80 (s, 3H), 3.68 (s, 3H), 3.58 (t, 1H), 3.03 (q, 2H), 2.99 (d, J=4.0 Hz,2H); MS (FD): m/e 376 (M+); Anal.: Calc'd. for C$_{24}$H$_{24}$O$_4$.0.25 mol H$_2$O: C, 75.67; H, 6.48; Found: C, 75.37; H, 6.63.

EXAMPLE 3

Preparation of [4-hydroxyphenyl] [1(3H)-2-(4-methoxyphenyl)-5-methoxy]indenyl]methane

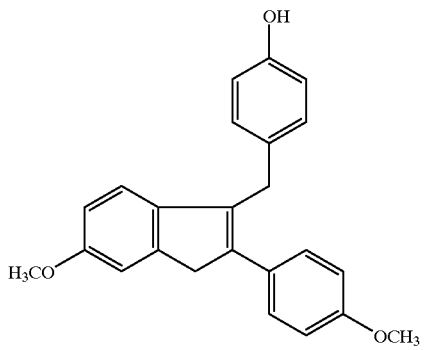

[4-Hydroxyphenyl] [1-hydroxy-2-(4-methoxyphenyl)-5-methoxy]indanyl]methane, (0.97 g, 2.5 mmol), prepared as described above in Example 2, was dissolved in 50 mL absolute ethanol which contained 10 mL 1N HCl and the resulting mixture was stirred at 25° C. for 45 minutes. The reaction mixture was then concentrated to dryness and the residue was distributed between ethyl acetate and water. The ethyl acetate layer was separated, dried over magnesium sulfate and concentrated to an oil. The oil was purified by chromatography over silica gel using hexane:ethyl acetate 7:3 to elute the product. Concentration of the fractions containing the product provided 0.54 g (61%) of amorphous product.

$^1$H NMR (CDCl$_3$): δ 7.38 (d, J=7.0 Hz, 2H), 7.17–7.03 (m, 3H), 7.00 (d, J=7.0 Hz, 1H), 6.90 (d, J=7.0 Hz, 2H), 6.80–6.75 (m, 3H), 4.60 (s, 1H), 4.00 (s, 2H), 3.83 (s, 6H), 3.80 (s, 2H); MS (FD): m/e 358 (M+); Anal.: Calc'd. for C$_{24}$H$_{22}$O$_3$: C, 80.42; H, 6.19; Found: C, 80.14; H, 6.22.

EXAMPLE 4

Preparation of 2-[4-[2-(1-piperidinyl)ethoxy]phenyl]-2-1[1-hydroxy-2-(4-methoxyphenyl)-5-methoxy]indanyl]-1,3-dithiane

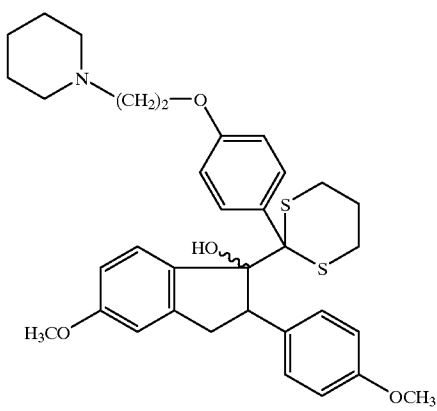

To a 250 mL 3 neck flame-dried round bottom flask under a nitrogen atmosphere was added 100 mL of anhydrous tetrahydrofuran and 2-[4-[2-(1-piperdinyl)ethoxy]phenyl]-1,3-dithiane], (1.70 g, 5.25 mmol). The resulting solution was cooled to −40° C. in an acetonitrile/dry ice bath and held at that temperature during the dropwise addition of n-butyl lithium (1.6 M, 3.5 mL, 5.25 mmol) in hexane. The resulting solution of the lithiated dithiane was kept at −40° C. and stirred for an additional 35 minutes. It was then cooled to near −78° C. in an acetone-dry ice bath. Then a solution of 2-(4-methoxyphenyl)-5-methoxy-1-indanone (1.40 g, 5.25 mmol) in 40 mL of anhydrous THF was added dropwise over 45 minutes. The resulting reaction mixture was still kept below −70° C. while it was stirred for 1.5 hr longer. Then the reaction was worked up by cautious addition of 100 mL of iced 1N HCl solution followed by evaporation of most of the THF. The resulting mixture was basified with 1N NaOH and the product was extracted into ethyl acetate. The ethyl acetate layer was separated and washed with additional 1N NaOH and finally with brine. Then it was dried over anhydrous magnesium sulfate and evaporated to an oil. The oil was purified using silica gel chromatography (Waters Prep 2000) and an elution gradient from toluene to 9:1 ethyl acetate:methanol containing 5% conc. ammonium hydroxide. Following concentration of the appropriate fractions, the desired product was isolated as 3.0 g (94%) of an amorphous solid.

$^1$H NMR (CDCl$_3$): δ 0.00 (d, J=0.0 Hz, 1H), 7.60 (s, 2H), 6.95 (d, J=7.0 Hz, 2H), 6.80–6.70 (m, 6H), 6.60 (s, 1H), 4.37 (s, 1H), 4.10 (m, 2H), 3.80 (s, 3H), 3.75 (s, 3H), 2.80 (m, 2H), 2.79–2.30 (m, 11H), 1.90 (m, 2H), 1.6 (m, 4H), 1.4 (m, 2H); MS (FD): m/e 592 (M+); Anal.: Calc'd. for C$_{34}$H$_{41}$NO$_4$S$_2$.0.25 mol H$_2$O: C, 69.00; H, 6.98; N, 2.37; Found: C, 68.99; H, 6.99; N, 2.40.

EXAMPLE 5

Preparation of [4-[2-(1-piperidinyl)ethoxy]phenyl] [1[1-hydroxy-2-(4-methoxyphenyl)-5-methoxy] indanyl]methane,

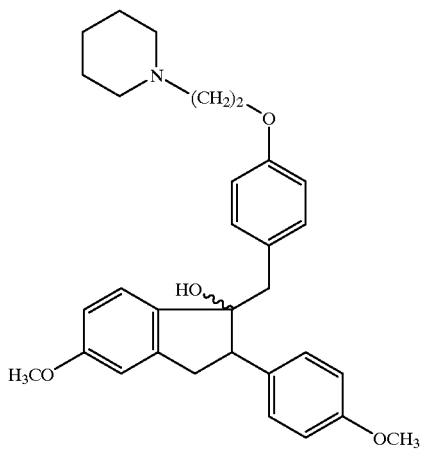

2-[4-[2-(1-Piperidinyl)ethoxy]phenyl]-2-[1-hydroxy-2-(4-methoxyphenyl)-5-methoxy]indanyl]-1,3-dithiane (5.0 g, 8.4 mmol) was dissolved in 275 mL absolute ethanol and 25 mL of 15M ammonium hydroxide. The solution was treated with 50 grams of Raney nickel, placed at an initial pressure of 60 psi under an atmosphere of hydrogen, and shaken overnight. The reaction mixture was then filtered through a pad of 1:1 talc and celite. Concentration of the filtrate provided an oil which was purified by radial chromatography over silica gel using 95:5 chloroform:methanol containing 0.25% (by volume) 15M ammonium hydroxide to elute the desired product which was obtained following concentration and drying as 3.0 g (76.9%) of a white amorphous solid:

$^1$H NMR (CDCl$_3$): δ 7.10–6.97 (m, 5H), 6.90–6.70 (m, 6H) 5.30 (s, 1H), 4.10 (m, 2H), 3.81 (s, 3H), 3.78 (s, 3H), 3.57 (s, 1H), 3.05 (q, 2H), 3.00 (s, 2H), 2.80 (m, 2H), 2.60–2.50 (m, 4H), 1.65–1.58 (m, 4H), 1.50–1.40 (m, 2H); MS (FD): m/e 487 (M+); Anal.: Calc'd. for C$_{31}$H$_{37}$NO$_4$: C, 76.36; H, 7.65; N, 2.87; Found: C, 76.50; H, 7.71; N, 2.85.

EXAMPLE 6

Preparation of [4-[2-(1-piperidinyl)ethoxy]phenyl] [1(3H)-2-(4-methoxyphenyl)-5-methoxy]indenyl] methane,

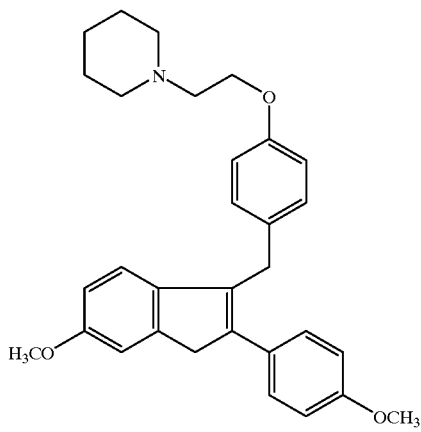

[4-[2-(1-Piperidinyl)ethoxy]phenyl] [1-hydroxy-2-(4-methoxyphenyl)-5-methoxy]indanyl]methane (2.30 g, 4.70 mmol), prepared as described above in Example 5, was dissolved in 200 mL absolute ethanol which contained 20 mL 5N HCl and the resulting mixture was stirred at 25° C. for 1 hr. The reaction mixture was treated with small volumes of saturated sodium bicarbonate solution until an excess had been added and gas evolution ceased. Then the resulting aqueous mixture was concentrated to remove the ethanol solvent. The product was extracted by ethyl acetate and the ethyl acetate layer was separated, washed with water, dried over magnesium sulfate and concentrated to an oil (1.8 g, 82%):

$^1$H NMR (CDCl$_3$): δ 7.35 (d, J=8.0 Hz, 2H) 7.15 (d, J=8.0 Hz, 2H), 7.07 (d, J=4.0 Hz, 1H), 7.00 (d, J=8.0 Hz, 1H), 6.90 (d, J=8.0 Hz, 2H), 6.80 (d, J=8.0 Hz, 2H), 6.75 (dd, J=6.0 Hz, 1H), 4.08 (t, 2H), 4.00 (s, 2H), 3.80 (s, 6H), 3.78 (s, 2H), 2.80 (t, 2H), 2.60–2.52 (m, 4H), 1.70–1.60 (m, 4H), 1.50–1.40 (m, 2H); MS (ion spray): m/e 470.6 (M+); Anal.: Calc'd. for C$_{31}$H$_{35}$NO$_3$: C, 79.28; H, 7.51; N, 2.98; Found: C, 79.00; H, 7.45; N, 2.53.

EXAMPLE 7

Preparation of [4-[2-(1-piperidinyl)ethoxy]phenyl] [1(3H)-2-(4-methoxyphenyl)-5-methoxy]indenyl] methane (Alternative Procedure)

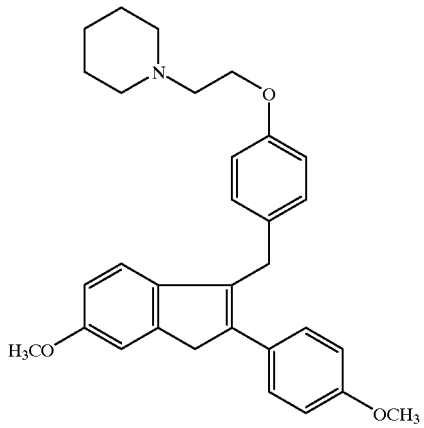

A flame-dried, 3-neck 50 mL flask was charged with a mixture of 48 mg (0.133 mmol) of [4-hydroxyphenyl] [1(3H)-2-(4-methoxyphenyl)-5-methoxy]indenyl]methane, cesium carbonate (200 mg, 0.6 mmol) and anhydrous DMF (15 mL), under an atmosphere of nitrogen. The mixture was stirred at ambient temperature for 20 min, and then 1-(2-chloroethyl)piperidine monohydrochloride (25 mg, 0.135 mmol) was added in one portion. Stirring was continued for 3 hr. The reaction mixture was then distributed between ethyl acetate and water. The organic layer was separated and washed five times with brine, dried over magnesium sulfate, filtered and concentrated to an amorphous residue. Although the product was not purified further and no yield was determined, NMR and mass spectral analysis confirm the major constituent to be identical to the product of Example 6.

EXAMPLE 8

Preparation of [4-[2-(1-piperidinyl)ethoxy]phenyl] [1(3H)-2-(4-hydroxyphenyl)-5-hydroxy]indenyl] methane hydrochloride

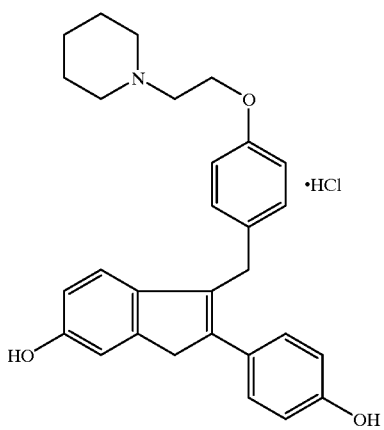

To a solution of [4-[2-(1-piperidinyl) ethoxy]-phenyl] [1(3H)-2-(4-methoxyphenyl)-5-methoxy]indenyl]methane, (0.920 g, 1.80 mmol) in 50 mL of anhydrous methylene chloride under $N_2$ at 0° C. was added boron tribromide (0.60 mL, 1.57 g, 6.30 mmol). The resulting mixture was kept cooled to near 0° C. while it was stirred for 1.5 hr. The reaction was then quenched by gradual addition of a large excess of cold saturated sodium bicarbonate (20 mL). When gas evolution ceased, the methylene chloride was removed under vacuum and the residual the aqueous layer was extracted with ethyl acetate. The organic layer was washed with additional saturated sodium bicarbonate solution, washed with water, dried (sodium sulfate), and concentrated in vacuo to an light reddish-orange oil. The crude free base was dissolved in 5 mL of methanol, 2 mL of 1N HCl was added, and the resulting solution was concentrated to dryness. Trituration by ethyl ether:ethyl acetate 1:1 induced the desired product to precipitate. The solid was collected and rinsed with additional ether, then dried in high vacuum at 25° C. overnight to provide 700 mg (84%).

$^1$H NMR (DMSO-$d_6$): δ 10.30 (s, 1H), 9.50 (s, 1H), 9.20 (s, 1H), 7.23 (d, J=7.0 Hz, 2H), 7.10 (d, J=7.0 Hz, 2H), 6.90–6.70 (m, 6H), 6.55 (d, J=7.0 Hz, 1H), 4.30 (m, 2H), 3.90 (s, 2H), 3.70 (s, 2H), 3.40 (m, 4H), 2.90 (m, 2H), 1.80–1.60 (m, 5H), 1.30 (m, 1H); MS (FD): m/e 442 (MH+ for the free base); Anal.: Calc'd. for $C_{29}H_{32}ClNO_3 \cdot 1.0$ mol EtOAc: C, 70.01; H, 7.12; N, 2.47; Found: C, 70.39; H, 6.93; N, 2.65.

Formulations

In the formulations which follow, "active ingredient" means a compound of formula I, or a salt or solvate thereof.

EXAMPLE 9

Preparation of a Gelatin Capsule Formulation

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

EXAMPLE 10

Preparation of Tablet Formulations

A tablet formulation is prepared using the ingredients below:

Tablet Formulation I

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets. Alternatively, tablets each containing 2.5–1000 mg of active ingredient are made up as follows:

Tablet Formulation II

| Ingredient | Quantity (mg/tablet) |
|---|---|
| Active ingredient | 2.5–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

EXAMPLE 11

Preparation of a Suspension Formulation

Suspensions each containing 0.1–1000 mg of medicament per 5 ml dose are made as follows:

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

EXAMPLE 12

Preparation of an Aerosol Formulation

An aerosol solution is prepared containing the following ingredients:

| Ingredient | Quantity (% by weight) |
|---|---|
| Active ingredient | 0.25 |
| Ethanol | 25.75 |
| Propellant 22 (Chlorodifluoromethane) | 74.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

EXAMPLE 13

Preparation of a Suppository Formulation

Suppositories are prepared as follows:

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

EXAMPLE 14

Preparation of a Parenteral Formulation

An intravenous formulation is prepared as follows:

| Ingredient | Quantity |
|---|---|
| Active ingredient | 50 mg |
| Isotonic saline | 1,000 mL |

The solution of the above ingredients is intravenously administered to a patient at a rate of about 1 mL per minute.

EXAMPLE 15

Preparation of Combination Formulations

Combination Capsule Formulation I

| Ingredient | Quantity (mg/capsule) |
|---|---|
| Active ingredient | 50 |
| Premarin ® | 1 |
| Avicel pH 101 | 50 |
| Starch 1500 | 117.50 |
| Silicon Oil | 2 |
| Tween 80 | 0.50 |
| Cab-O-Sil | 0.25 |

Combination Capsule Formulation II

| Ingredient | Quantity (mg/capsule) |
|---|---|
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Combination Tablet Formulation

| Ingredient | Quantity (mg/capsule) |
|---|---|
| Active ingredient | 50 |
| Premarin ® | 1 |

-continued

| Ingredient | Quantity (mg/capsule) |
| --- | --- |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

We claim:

1. A compound of formula I:

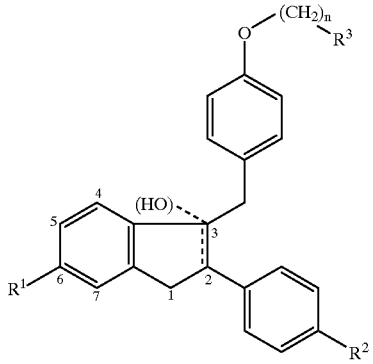

or a pharmaceutically acceptable salt thereof wherein
$R^1$ is selected from the group consisting of
—H,
—OH,
—O($C_1$–$C_4$ alkyl),
—OCO($C_1$–$C_6$ alkyl),
—OSO$_2$($C_2$–$C_6$ alkyl), and
—OCOAr wherein Ar is unsubstituted phenyl or is phenyl substituted with one or more substituents independently selected from the group consisting of
$C_1$–$C_4$ alkyl,
$C_1$–$C_4$ alkoxy,
halo, and
hydroxy;
$R^2$ is selected from the group consisting of
—H,
—OH,
—O($C_1$–$C_4$ alkyl),
—OCO($C_1$–$C_6$ alkyl),
—OSO$_2$($C_2$–$C_6$ alkyl),
—OCOAr wherein Ar is as defined above, and halo;
$R^3$ is selected from the group consisting of
1-piperidinyl,
1-pyrrolidinyl,
methyl-1-pyrrolidinyl,
dimethyl-1-pyrrolidinyl,
4-morpholino,
dimethylamino,
diethylamino,
diisopropylamino, and
1-hexamethyleneimino;
n is 2 or 3; and the dashed line bond between the carbon atoms at positions 1 and 2 of the indene nucleus represents an optional double bond with the proviso that when the double bond is absent, the parenthetic hydroxy group at position 1 is present, and when the double bond is present, the parenthetic hydroxy group at position 1 is absent.

2. A compound according to claim 1 having the structural formula:

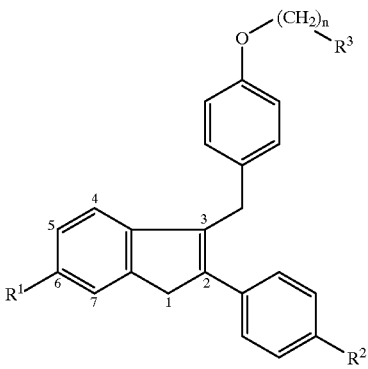

wherein $R^1$ is selected from the group consisting of
—H,
—OH,
—O($C_1$–$C_4$ alkyl),
—OCO($C_1$–$C_6$ alkyl),
—OSO$_2$($C_2$–$C_6$ alkyl), and
—OCOAr wherein Ar is unsubstituted phenyl or is phenyl substituted with one or more substituents independently selected from the group consisting of
$C_1$–$C_4$ alkyl,
$C_1$–$C_4$ alkoxy,
halo, and
hydroxy;
$R^2$ is selected from the group consisting of
—H,
—OH,
—O($C_1$–$C_4$ alkyl),
—OCO($C_1$–$C_6$ alkyl),
—OSO$_2$($C_2$–$C_6$ alkyl),
—OCOAr wherein Ar is as defined above, and halo;
$R^3$ is selected from the group consisting of
1-piperidinyl,
1-pyrrolidinyl,
methyl-1-pyrrolidinyl,
dimethyl-1-pyrrolidinyl,
4-morpholino,
dimethylamino,
diethylamino,
diisopropylamino, and
1-hexamethyleneimino;
and n is 2 or 3.

3. A compound according to claim 1 having the structural formula:

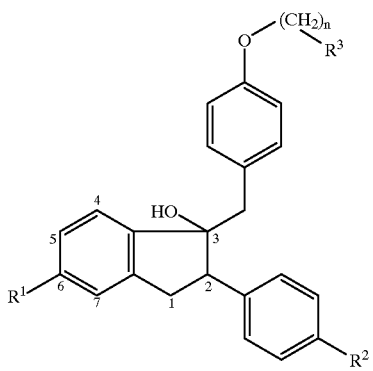

wherein R¹ is selected from the group consisting of
- —H,
- —OH,
- —O($C_1$–$C_4$ alkyl),
- —OCO($C_1$–$C_6$ alkyl),
- —O$SO_2$($C_2$–$C_6$ alkyl), and
- —OCOAr wherein Ar is unsubstituted phenyl or is phenyl substituted with one or more substituents independently selected from the group consisting of
  - $C_1$–$C_4$ alkyl,
  - $C_1$–$C_4$ alkoxy,
  - halo, and
  - hydroxy;

R² is selected from the group consisting of
- —H,
- —OH,
- —O($C_1$–$C_4$ alkyl),
- —OCO($C_1$–$C_6$ alkyl),
- —O$SO_2$($C_2$–$C_6$ alkyl),
- —OCOAr wherein Ar is as defined above, and halo;

R³ is selected from the group consisting of
- 1-piperidinyl,
- 1-pyrrolidinyl,
- methyl-1-pyrrolidinyl,
- dimethyl-1-pyrrolidinyl,
- 4-morpholino,
- dimethylamino,
- diethylamino,
- diisopropylamino, and
- 1-hexamethyleneimino;

and n is 2 or 3.

4. A compound selected from the group consisting of compounds of formulae II and III:

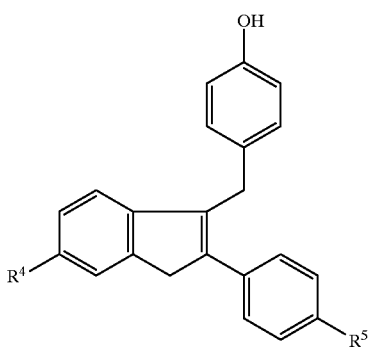

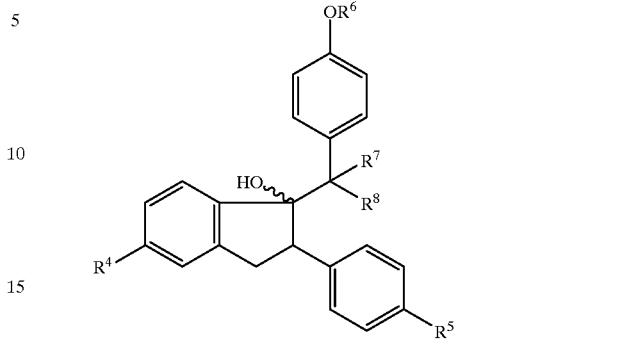

wherein
R⁴ and R⁵ are protected hydroxy groups;
R⁶ is selected from the group consisting of
hydrogen, benzyl, and
—O($CH_2$)$_n$R³, wherein R³ is selected from the group consisting of
- 1-piperidinyl,
- 1-pyrrolidinyl,
- methyl-1-pyrrolidinyl,
- dimethyl-1-pyrrolidinyl,
- 4-morpholino,
- dimethylamino,
- diethylamino,
- diisopropylamino, and
- 1-hexamethyleneimino; and R⁷ and R⁸ are both hydrogen or —SR¹⁰ wherein R¹⁰ is methyl or ethyl, or R⁷ and R⁸, taken together with the carbon atom to which they are attached form a ring having the formula

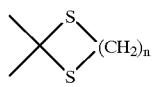

wherein n is 2 or 3;
with the proviso that when R⁶ is hydrogen, R⁴ and R⁵ are also hydrogen.

5. A compound according to claim 1 or a pharmaceutically acceptable salt thereof wherein R¹ and R² are independently selected from hydroxy and $C_1$–$C_4$ alkoxy, and n is 2.

6. A compound according to claim 5 wherein R³ is selected from the group consisting of 1-pyrrolidinyl and 1-piperidinyl.

7. A compound according to claim 1 or a pharmaceutically acceptable salt thereof selected from the group consisting of
- 6-hydroxy-2-phenyl-3-[(4-(2-pyrrolidin-1-yl-ethoxy)-phenyl)methyl]-1H-indene;
- 6-methoxy-2-phenyl-3-[(4-(2-pyrrolidin-1-yl-ethoxy)-phenyl)methyl]-1H-indene;
- 6-hydroxy-2-(4-hydroxyphenyl)-3-[(4-(2-pyrrolidin-1-yl-ethoxy)phenyl)methyl]-1H-indene;
- 6-hydroxy-2-(4-methoxyphenyl)-3-[(4-(2-pyrrolidin-1-yl-ethoxy)phenyl)methyl]-1H-indene;
- 6-methoxy-2-(4-methoxyphenyl)-3-[(4-(2-pyrrolidin-1-yl-ethoxy)phenyl)methyl]-1H-indene;
- 6-hydroxy-2-(4-hydroxyphenyl)-3-[(4-(2-piperidin-1-yl-ethoxy)phenyl)methyl]-1H-indene;

6-hydroxy-2-(4-methoxyphenyl)-3-[(4-(2-piperidin-1-yl-ethoxy)phenyl)methyl]-1H-indene;

6-methoxy-2-(4-methoxyphenyl)-3-[(4-(2-piperidin-1-yl-ethoxy)phenyl)methyl]-1H-indene;

6-acetoxy-2-phenyl-3-[(4-(2-pyrrolidin-1-yl-ethoxy)-phenyl)methyl]-1H-indene;

6-benzoyloxy-2-phenyl-3-[(4-(2-pyrrolidin-1-yl-ethoxy)-phenyl)methyl]-1H-indene;

6-methylsulfonyloxy-2-phenyl-3-[(4-(2-pyrrolidin-1-yl-ethoxy)phenyl)methyl]-1H-indene;

6-acetoxy-2-phenyl-3-[(4-(2-piperidin-1-yl-ethoxy)-phenyl)methyl]-1H-indene;

6-benzoyloxy-2-phenyl-3-[(4-(2-piperidin-1-yl-ethoxy)-phenyl)methyl]-1H-indene;

6-methylsulfonyloxy-2-phenyl-3-[(4-(2-piperidin-1-yl-ethoxy)phenyl)methyl]-1H-indene;

6-hydroxy-2-(4-acetoxyphenyl)-3-[(4-(2-pyrrolidin-1-yl-ethoxy)phenyl)methyl]-1H-indene;

6-hydroxy-2-(4-benzoyloxyphenyl)-3-[(4-(2-pyrrolidin-1-yl-ethoxy)phenyl)methyl]-1H-indene;

6-hydroxy-2-(4-methylsulfonyloxyphenyl)-3-[(4-(2-pyrrolidin-1-yl-ethoxy)phenyl)methyl]-1H-indene;

6-hydroxy-2-(4-acetoxyphenyl)-3-[(4-(2-piperidin-1-yl-ethoxy)phenyl)methyl]-1H-indene;

6-hydroxy-2-(4-benzoyloxyphenyl)-3-[(4-(2-piperidin-1-yl-ethoxy)phenyl)methyl]-1H-indene; and 6-hydroxy-2-(4-methylsulfonyloxyphenyl)-3-[(4-(2-piperidin-1-yl-ethoxy)phenyl)methyl]-1H-indene; or a pharmaceutically acceptable salt thereof.

8. A compound according to claim 6 selected from the group consisting of 6-hydroxy-2-(4-hydroxyphenyl)-3-[(4-(2-piperidin-1-yl-ethoxy)phenyl)methyl]-1H-indene;

6-hydroxy-2-(4-methoxyphenyl)-3-[(4-(2-piperidin-1-yl-ethoxy)phenyl)methyl]-1H-indene; and 6-methoxy-2-(4-methoxyphenyl)-3-[(4-(2-piperidin-1-yl-ethoxy)phenyl)methyl]-1H-indene; or a pharmaceutically acceptable salt thereof.

9. A compound according to claim 4 selected from the group consisting of 2,3-dihydro-3,6-dihydroxy-2-phenyl-3-[(4-(2-pyrrolidin-1-yl-ethoxy)phenyl)methyl]-1H-indene;

2,3-dihydro-3-hydroxy-6-methoxy-2-phenyl-3-[(4-(2-pyrrolidin-1-yl-ethoxy)phenyl)methyl]-1H-indene;

2,3-dihydro-3,6-dihydroxy-2-(4-hydroxyphenyl)-3-[(4-(2-pyrrolidin-1-yl-ethoxy)phenyl)methyl]-1H-indene;

2,3-dihydro-3,6-dihydroxy-2-(4-methoxyphenyl)-3-[(4-(2-pyrrolidin-1-yl-ethoxy)phenyl)methyl]-1H-indene;

2,3-dihydro-3,6-dihydroxy-2-(4-hydroxyphenyl)-3-[(4-(2-piperidin-1-yl-ethoxy)phenyl)methyl]-1H-indene;

2,3-dihydro-3,6-dihydroxy-2-(4-methoxyphenyl)-3-[(4-(2-piperidin-1-yl-ethoxy)phenyl)methyl]-1H-indene;

2,3-dihydro-3-hydroxy-6-acetoxy-2-phenyl-3-[(4-(2-pyrrolidin-1-yl-ethoxy)phenyl)methyl]-1H-indene;

2,3-dihydro-3-hydroxy-6-benzoyloxy-2-phenyl-3-[(4-(2-pyrrolidin-1-yl-ethoxy)phenyl)methyl]-1H-indene;

6-methylsulfonyloxy-2-phenyl-3-[(4-(2-pyrrolidin-1-yl-ethoxy)phenyl)methyl]-1H-indene;

6-acetoxy-2-phenyl-3-[(4-(2-piperidin-1-yl-ethoxy)-phenyl)methyl]-1H-indene;

6-benzoyloxy-2-phenyl-3-[(4-(2-piperidin-1-yl-ethoxy)-phenyl)methyl]-1H-indene;

6-methylsulfonyloxy-2-phenyl-3-[(4-(2-piperidin-1-yl-ethoxy)phenyl)methyl]-1H-indene;

6-hydroxy-2-(4-acetoxyphenyl)-3-[(4-(2-pyrrolidin-1-yl-ethoxy)phenyl)methyl]-1H-indene;

6-hydroxy-2-(4-benzoyloxyphenyl)-3-[(4-(2-pyrrolidin-1-yl-ethoxy)phenyl)methyl]-1H-indene;

5-hydroxy-2-(4-methylsulfonyloxyphenyl)-3-[(4-(2-pyrrolidin-1-yl-ethoxy)phenyl)methyl]-1H-indene;

6-hydroxy-2-(4-acetoxyphenyl)-3-[(4-(2-piperidin-1-yl-ethoxy)phenyl)methyl]-1H-indene;

6-hydroxy-2-(4-benzoyloxyphenyl)-3-[(4-(2-piperidin-1-yl-ethoxy)phenyl)methyl]-1H-indene; and 6-hydroxy-2-(4-methylsulfonyloxyphenyl)-3-[(4-(2-piperidin-1-yl-ethoxy)phenyl)methyl]-1H-indene.

10. A pharmaceutical composition comprising a therapeutically effective amount of a compound as defined by claim 1 in combination with a pharmaceutically acceptable carrier, excipient or diluent.

11. A method of treating osteoporosis in a woman in need of such treatment comprising administering an effective amount of a compound according to claim 1.

12. A method of treating hyperlipidemia resulted from estrogen deficiency in a woman in need of such treatment comprising administering an effective amount of a compound according to claim 1.

* * * * *